United States Patent [19]

Fries et al.

[11] Patent Number: 5,784,424
[45] Date of Patent: Jul. 21, 1998

[54] SYSTEM FOR STUDYING A SAMPLE OF MATERIAL USING A HEAVY ION INDUCED MASS SPECTROMETER SOURCE

[75] Inventors: David P. Fries, St. Petersburg; James F. Browning, Palm Harbour, both of Fla.

[73] Assignee: The United States of America as represented by the United States Department of Energy, Washington, D.C.

[21] Appl. No.: 674,970

[22] Filed: Jul. 3, 1996

Related U.S. Application Data

[63] Continuation of Ser. No. 312,907, Sep. 30, 1994, abandoned.
[51] Int. Cl.$^6$ .............................. G21G 1/08; B01D 59/44
[52] U.S. Cl. ..................... 376/189; 376/119; 376/159; 376/170; 250/287
[58] Field of Search ......................... 376/159, 189, 376/190, 192–195, 346, 341, 154, 110, 115, 119, 158, 170; 250/281–283, 287, 390.07, 390.08, 390.09

[56] References Cited

U.S. PATENT DOCUMENTS

| | | | |
|---|---|---|---|
| 3,031,394 | 4/1962 | McCorkle et al. | 376/341 |
| 3,291,694 | 12/1966 | Borst | 376/346 |
| 3,423,844 | 1/1969 | Mittelman | 376/100 |
| 3,496,357 | 2/1970 | Weinziel et al. | 376/159 |
| 3,976,888 | 8/1976 | Miller et al. | 376/170 |
| 4,240,844 | 12/1980 | Felice et al. | 148/1.5 |
| 4,300,054 | 11/1981 | Dance et al. | 376/190 |
| 4,314,155 | 2/1982 | Sowerby | 376/159 |
| 4,490,610 | 12/1984 | Ulbricht, Jr. | 250/287 |
| 4,578,237 | 3/1986 | Mordarski et al. | 376/154 |
| 4,634,568 | 1/1987 | Wimpee et al. | 376/154 |
| 4,694,168 | 9/1987 | Beyee et al. | 250/287 |
| 4,830,913 | 5/1989 | Dance | 376/110 |
| 4,835,383 | 5/1989 | Mahoney et al. | |
| 4,857,259 | 8/1989 | Bartko et al. | 376/154 |
| 4,938,916 | 7/1990 | Dance | 376/110 |
| 5,002,720 | 3/1991 | Berggren | 376/154 |
| 5,078,951 | 1/1992 | August, Jr. | 376/154 |
| 5,135,704 | 8/1992 | Shefer et al. | 376/110 |
| 5,148,021 | 9/1992 | Okamoto et al. | |
| 5,232,711 | 8/1993 | Sanderson et al. | |
| 5,360,976 | 11/1994 | Young et al. | 250/281 |

OTHER PUBLICATIONS

Kerntechnik, vol 17, No. 1, (1975), pp. 36–41.
Nuclear Technology, vol. 10 (Mar. 1971), pp. 365–379, Menlove et al.
Macfarlane, 252 Cf-Plasma desorption mass spectrometry using polymer surfaces, published in "Trends in Analytical Chemistry", vol. 7, No. 5, 1988, pp. 179–183.
Cotter, Plasma Desorption Mass Spectrometry: Coming of Age, published in "Analytical Chemistry", vol. 60, No. 13, Jul. 1, 1988, pp. 781 A, 782 A, 784 A, 786 A, 788 A, 789 A, 791 A, 793 A.

*Primary Examiner*—Harvey E. Behrend
*Attorney, Agent, or Firm*—Armand McMillan; William R. Moser; Paul A. Gottlieb

[57] ABSTRACT

A heavy ion generator is used with a plasma desorption mass spectrometer to provide an appropriate neutron flux in the direction of a fissionable material in order to desorb and ionize large molecules from the material for mass analysis.

The heavy ion generator comprises a fissionable material having a high n,f reaction cross section. The heavy ion generator also comprises a pulsed neutron generator that is used to bombard the fissionable material with pulses of neutrons, thereby causing heavy ions to be emitted from the fissionable material. These heavy ions impinge on a material, thereby causing ions to desorb off that material. The ions desorbed off the material pass through a time-of-flight mass analyzer, wherein ions can be measured with masses greater than 25,000 amu.

19 Claims, 3 Drawing Sheets

SYSTEM FOR STUDYING A SAMPLE OF MATERIAL USING A HEAVY ION INDUCED MASS SPECTROMETER SOURCE

This application is a continuation of application Ser. No. 08/312,907, filed Sep. 30, 1994, now abandoned.

The United States Government has rights in this invention pursuant to contract no. DE-AC04-92AL73000 between the United States Department of Energy and Martin Marietta Specialty Components, Inc.

BACKGROUND OF THE INVENTION

1. Field of the Invention

The invention relates to a plasma desorption mass spectrometer source. In particular, the invention relates to a plasma desorption mass spectrometer source which contains a pulsed neutron generator to provide an appropriate neutron flux in the direction of a fissionable material producing a pulsed source of heavy ions in order to desorb and ionize large molecules from a material for mass analysis.

2. Description of the Related Art

Accurate determination of molecular weights of biomolecules, such as proteins, is very important in biochemistry and industrial polymer applications as an analytical tool for molecular characterization. The molecular weight is a useful parameter, since it is indicative of the size of a biomolecule and gives an approximation of the number and type of subunits constituting the biomolecule. Of particular importance is the analysis of special proteins used in recombinant DNA research, where the paramount criteria of identity from one protein to another protein is the molecular weight of each protein.

The molecular weight of proteins ranges from 10,000 atomic mass units (amu) to over 500,000 amu. Mass spectrometry is one method used for providing an accurate determination of weights of biomolecules involving large masses. However, conventional mass spectrometers are only useful for measuring molecular weights up to about 25,000 amu.

Mass spectrometry involves three distinct functions: sample ionization, mass analysis and ion detection. FIG. 1 illustrates the high-level structural features of a mass spectrometer, whereby an ion beam 10-1 is provided by an ion source 20-1. The ion beam then passes through a mass analyzer 30-1, which separates the ions based on their charge-to-mass ratios. Such a mass analyzer 30-1 may be of the quadrupole type, magnetic sector type, or time of flight (TOF) type. Both the (quadrupole and magnetic sector mass analyzer systems have inherent limitations, however, due to the requirements of larger mass analyzer size for measuring larger ion masses. TOF mass analyzers allow for high molecular mass range, high ion transmission, and have the ability to record ions of different mass simultaneously. Therefore, TOF mass analyzers are preferred devices for analyzing large mass biomolecules. After passing through the TOF mass analyzer 30-1, the ion beam 10-1 arrives at the ion detector 40-1. For TOF spectrometers, the time that an ion arrives at the detector ion 40-1 serves as an indication of the mass of the ion.

Based on improvements in each of the three distinct functions of a mass spectrometer, accurate results can be achieved for measurements of biomolecules of masses below 10,000 amu, and reasonably effective measurements have been performed using Plasma Desorption Mass Spectrometry (PDMS), Matrix Assisted Laser Desorption Mass Spectrometry (MALDI), and Electro-Spray Mass Spectrometry (ESMS), for proteins as large as 25,000 amu. However, at present, both MALDI and ESMS are experiencing technical evolutions to allow for the detection of ions in the mass range of 25,000–500,000 amu.

The original method used in mass spectrometry for detecting heavy molecules utilized primary ions from a radioactive source that traveled at high velocities and which subsequently impacted on a thin film of a sample of interest. This impact then caused a subsequent ejection, or desorption, of secondary ions from that thin film. The term "desorption" means the removal of ions from a surface. These secondary ions were subsequently mass differentiated and detected. PDMS is the original large molecule detecting mass spectrometry technique. A general background of this technology is given by Robert Cotter, in Plasma Desorption Mass Spectrometry: Coming of Age, in *Analytical Chemistry*, Vol. 60, No. 13, Jul. 1, 1988. A block diagram of a plasma desorption mass spectrometer is shown in FIG. 2. The typical ionization source that is utilized is a 10-µCi sample of $^{252}$Cf (californium), which is held between two thin sheets of nickel foil. The ionization source is held at the same electrical potential (around 20 kV) as the sample to be analyzed. $^{252}$Cf is used as the source since it has a high probability for spontaneous fission.

$^{252}$Cf decays with a half-life of 2.65 years, of which 97% is decayed as alpha particles and 3% is decayed by spontaneous fission. That is, 3% is decayed as two charged fragments simultaneously emitted in opposite directions, 180 degrees apart from each other. Typically, such a decay involves $^{106}$Tc and $^{142}$Ba, with a total energy of about 200 million electron volts (MeV) and with a total mass of about 200 amu.

At the start of each timing cycle, one of the fission fragments hits a start detector 10-2, which is constructed as a grounded foil that emits secondary electrons collected by a dual channel plate detector 20-2. The output pulse from the detector 20-2 is amplified by amplifier 30-2, passed through a constant fraction discriminator 40-2, and recorded as the start pulse by a time-to-digital converter 50-2. The detector foil 10-2 and the discriminator 40-2 are designed to distinguish fission fragments from lower energy alpha particles, which emit about 6.1 MeV of energy per alpha particle. Discriminator 40-2 only provides an output for energies above the alpha particle energy and is thus responsive selectively to the fission fragments.

At the same time that the first fission fragment impinges the detector foil 10-2, the second fission fragment penetrates sample stage 60-2 (typically made of aluminum) on which sample 70-2 has been deposited on the reverse side thereof.

As a result of their masses and high velocities, the fission fragments emitted from the $^{252}$Cf source are able to deposit large amounts of energy as they impinge on the sample 70-2 on the foil 60-2, allowing for the desorption of high molecular weight species from the sample 70-2.

Typically, from 1 to 10 high molecular weight secondary ions are desorbed from the sample 70-2 and accelerated toward a grid 80-2 held at ground potential, where the secondary ions enter a long (15 cm to 3 m) drift region 90-2 with velocities inversely proportional to the square root of their masses. The amount of time needed to travel through the drift region 90-2 is a function of the mass of each particle desorbed from the sample 70-2.

These particles are then detected by a detector 100-2; the detector output signals are amplified by an amplifier 110-2, and passed through a constant fraction discriminator 120-2. The output signal from the discriminator is fed to the time-to-digital converter 50-2. The data from the first and second fission fragments are then sent to a processor, such as a computer 130-2, which determines a mass spectrum based on this data.

As noted above, a californium source produces heavy ions, but it does so in a not-very-predictable manner. Another limitation of using the californium source is the low yield of molecular ions. Still another problem with using the californium source is that, since the alpha particles that are emitted are of much lower momentum than the particles emitted by spontaneous fission, the alpha particles greatly increase the number of fragmented ions, and since there is no time correlation for the alpha particle-initiated events, the signal-to-noise ratio levels are markedly decreased. All of these problems contribute to long acquisition times and decreased molecular ion sensitivity.

Therefore, it is desired to find a better source for use in a plasma desorption mass spectrometer, and especially a source useful in measuring molecular weights greater than 25,000 amu.

SUMMARY OF THE INVENTION

According to the invention, a pulsed neutron generator and a uranium foil are used with a plasma desorption mass spectrometer to increase the detection characteristics of large size molecules being analyzed.

Accordingly, an object of the invention is to provide a heavy ion generator comprising a fissionable material having an n,f reaction cross-section greater than a predetermined value, and a pulsed neutron generator positioned to bombard the fissionable material with neutrons thereby producing heavy ions emitted from the fissionable material in a fashion following the pulse form of the neutron burst.

Another object of the invention is to provide a heavy ion generator as described above, wherein the pulsed neutron generator has an adjustable repetition rate for generating pulses.

The invention is directed toward a system for studying a sample of material. This system comprises a heavy ion generator which further comprises a pulsed neutron generator and a fissionable material having an n,f reaction cross-section greater than a predetermined value. The pulsed neutron generator is positioned to bombard the fissionable material with neutrons to thereby produce heavy ions emitted from the fissionable material. At least some of the heavy ions propagate toward and fall incident upon the sample of material, thereby inducing desorption of the sample.

The invention is also directed toward a method for studying a sample of material. The first step of the method involves placing a 238 isotope of uranium ($^{238}$U) in a path of a pulsed neutron generator. The second step involves placing the sample of material near the $^{238}$U source. The third step involves generating one or more neutron pulses by the neutron pulse generator, thereby causing at least one or more heavy ions to be emitted from the $^{238}$U source, and thereby causing at least one of the one or more heavy ions to fall incident upon the sample of material, which induces desorption of at least one ion off the sample of material.

BRIEF DESCRIPTION OF THE DRAWINGS

The invention is set forth with particularity in the appended claims. The invention, together with further objects and advantages thereof, may best be understood by making reference to the following description taken in conjunction with the accompanying drawings wherein:

DETAILED DESCRIPTION OF THE PREFERRED EMBODIMENT

Figure 1:
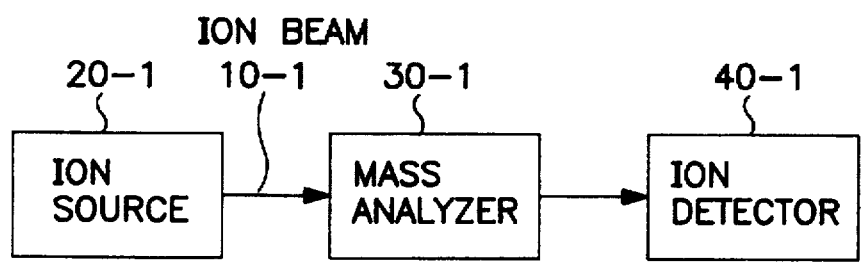
FIG. 1 is a high level block diagram of the components making up a conventional mass spectrometer.
Figure 2:
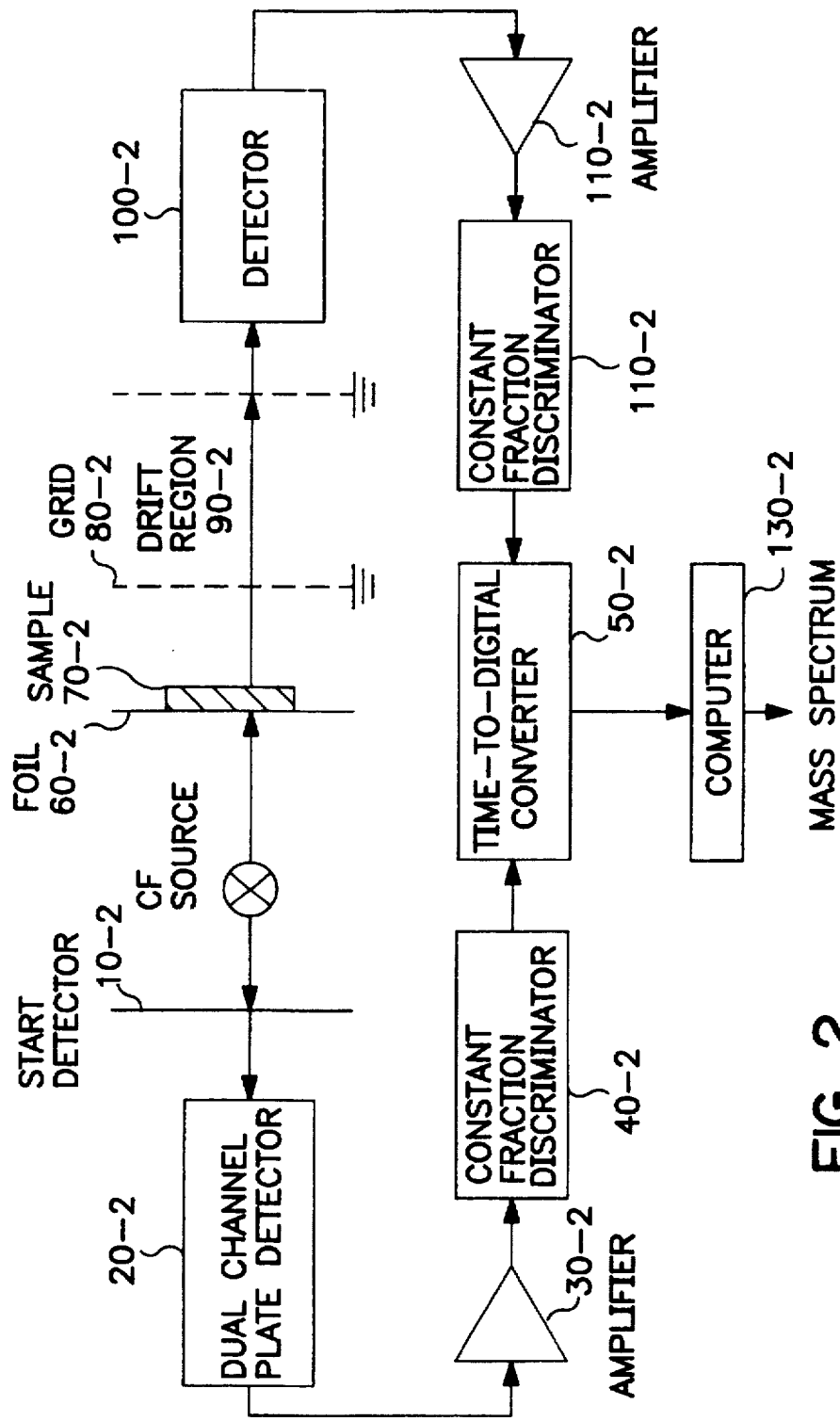
FIG. 2 is a block diagram of a conventional time of flight mass spectrometer.

As noted above, a californium source produces heavy ions in a not-so-predictable manner. Thus, a feature of the invention is the generation of heavy molecular ions in a predictable or controllable way. According to the invention, a uranium 238 ($^{238}$U) foil is bombarded with neutrons from a pulsed neutron generator. The neutrons contact the foil and because of the high (n,f) reaction cross-section (neutron to fission fragment cross-section) of $^{238}$U, heavy ions come off. The pulsed neutron generator has an adjustable repetition rate, or pulse rate, such that timing information that correlates the masses of heavy molecular ions can be extracted. With this timing information, the heavy molecular ion generation can be characterized and used more effectively in studying a substance.

The invention as described herein takes advantage of the n,f reaction in the 238 isotope of uranium. In doing so, the reliance on the random break-up of californium is removed. In the system according to the invention, fission fragment generation is directly related to the neutron burst. That is, the time mark for the secondary desorption event, which corresponds to the desorption of ions from the sample, can be related to the timing of the neutron pulse that caused the primary emission event. A burst of neutrons from a pulsed neutron generator is allowed to impinge on a $^{238}$U foil, causing multiple fission events. Of these, a considerable number of fission fragments called primary ions will propagate toward and fall incident on the thin-film sample target, thereby inducing desorption of the sample target. These multiple fission events occur at a rate of several orders of magnitude (i.e., hundreds or thousands), and cause desorption of the heavy ions from the sample target. This results in multiple, time-correlated events instead of the single time-correlated event of a spontaneous fission using the californium source. In some cases, it will be possible to reduce acquisition times from hours to minutes or even seconds by using the $^{238}$U source. Also, it is possible to optimize TOF windows, as well as the number of pulse cycles, by varying pulse parameters appropriately.

According to one embodiment of the invention, a mass spectrometer source contains a pulsed neutron generator with associated control electronics to provided an appropriate neutron flux in the direction of a fissionable material with a high-enough n,f reaction cross-section. The preferred fissionable material is $^{238}$U. Resultant fission fragments, hereafter referred to as primary ions, are then used to desorb heavy molecular ions from a target. The desorbed ions are hereinafter referred to as secondary ions. These secondary ions are then analyzed by a TOF mass discriminator. The timing sequence allowing for TOF mass discrimination, and any decay particle suppressions are associated with the timing sequence of the neutron pulses, resulting in a significantly improved degree of correlation between primary ion generation, secondary ion generation, and detection.

Figure 3:
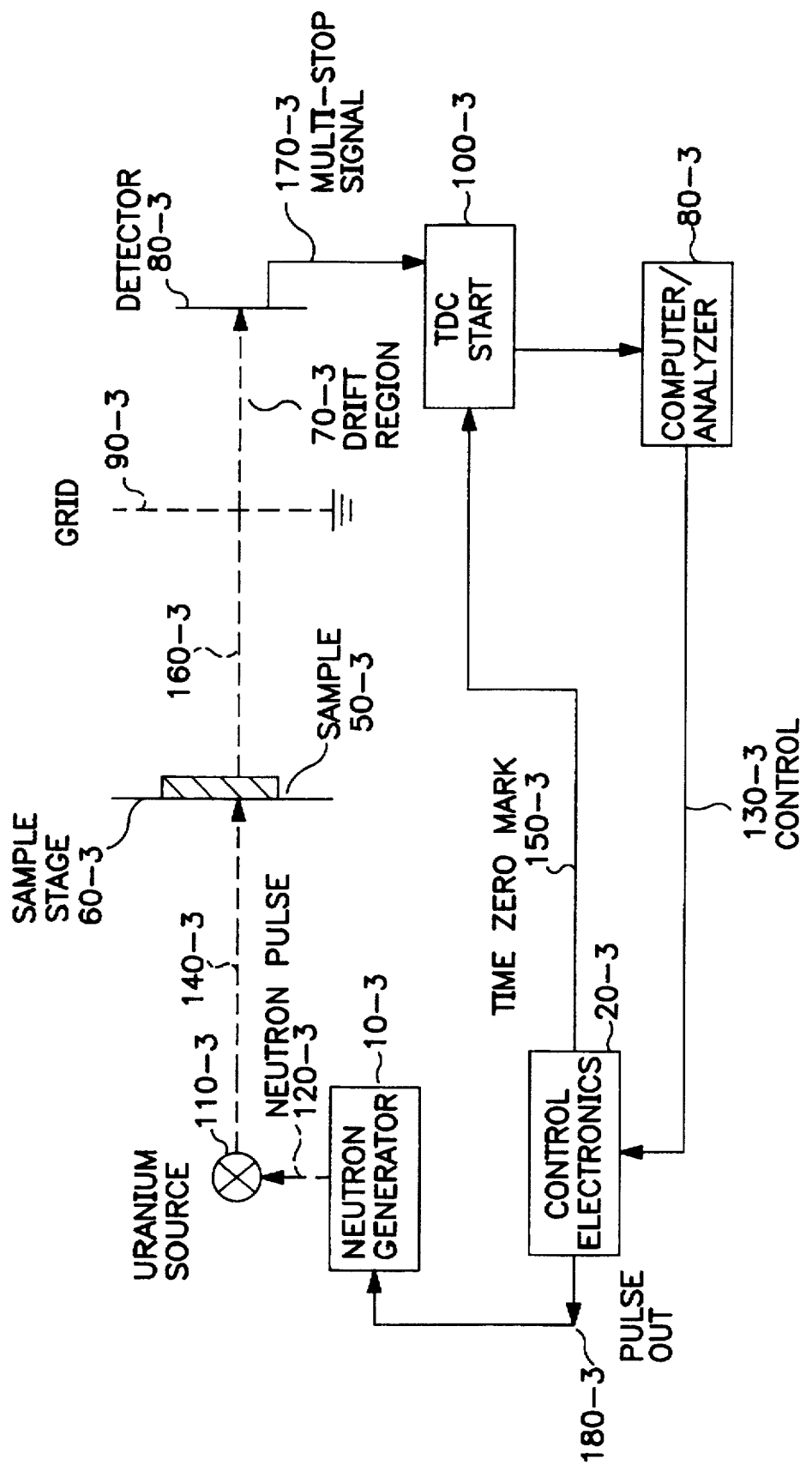
FIG. 3 is a block diagram of a mass spectrometer according to an embodiment of the invention.

A block diagram of a preferred embodiment of the invention is given in FIG. 3. Neutron pulses are sent to a $^{238}$U source 110-3 by a neutron generator 10-3. The number and rate of the neutron pulses 120-3 emitted from the neutron source 10-3 are controlled by pulse out signals 180-3 sent by the control electronics 20-3. The control electronics 20-3 are controlled by control signals 130-3 sent by a computer/ analyzer 40-3. By way of example but not by way of limitation, in the preferred embodiment, the computer/ analyzer 40-3 can be an IBM-compatible personal computer. As a result of the bombardment of the $^{238}$U source 110-3 by the neutron pulses 120-3, heavy mass ions (also called fission fragments) 140-3 are emitted from the $^{238}$U source 110-3 at a controllable and predictable rate. There is no need to use a complement particle as a time mark (as is done with californium as the radioactive source), since a time zero mark signal 150-3 is sent from the control electronics 20-3 to a Time-to-Digital Converter (TDC) 100-3 in coincidence with each burst of neutron pulses 120-3 emitted from the neutron generator 10-3. The fission fragments 140-3 emitted from the $^{238}$U source 110-3 due to the neutron pulses 120-3 hit the sample stage 60-3. These fission fragments 140-3 then pass through the sample stage 60-3, and impinge on the thin film sample 50-3 attached on one side of the sample stage 60-3. The sample stage 60-3 is positioned close to the $^{231}$U source 110-3, such that a substantial majority of the fission fragments 140-3 emitted from the $^{238}$U source 110-3 will impinge on the sample 50-3. With the closeness in location between the $^{238}$U source and the sample stage 60-3, the solid angle of the dispersal of the fission fragments 140-3 being ionized from the $^{238}$U source will not present a problem with respect to a certain percentage of the fission fragments 140-3 missing the sample stage 60-3.

As a result of their masses and high velocities, some of the fission fragments emitted from the $^{238}$U source are able to deposit large amounts of energy as they impinge on the thin film sample 50-3, allowing for the desorption of high molecular weight species from the sample 50-3. Molecules 160-3 are desorbed off the thin film sample 50-3 and accelerate toward a grid 90-3 held at a fixed potential, typically a ground potential. The grid 90-3 may be made of any of several standard types of grid material, such as a screen material. The desorbed molecules 160-3 then enter a drift region 70-3 with velocities inversely proportional to the square root of their masses. The amount of time needed to travel through the drift region 70-3 determines the mass of each particle desorbed from the thin film sample 50-3. When the desorbed molecules 160-3 exit from the sample 50-3, each of the desorbed molecules 160-3 have a relatively small amount of energy associated with them, typically around 100 electron volts (eV) of kinetic energy. These low energy particles will typically be desorbed off the sample 50-3 in various directions. However, as these desorbed molecules 160-3 get pulled into the drift region 70-3 by the attraction to the high potential at the grid 90-3, the desorbed molecules 160-3 will be pulled in line, so that the desorbed molecules 160-3 will travel through the drift region 70-3 in essentially parallel paths with respect to each other. The high potential at the grid 90-3 causes the desorbed molecules 160-3 to be accelerated towards the grid 90-3, where the desorbed molecules 160-3 then pass through the grid 90-3, and enter a field-free region, also known as the drift region 70-3. In the drift region 70-3, there are no forces acting upon the desorbed molecules 160-3, and so the heavier ones of the desorbed molecules 160-3 lag behind the lighter ones of the desorbed molecules 160-3, due to the fact that each of the desorbed molecules 160-3 enters the drift region 70-3 with the same kinetic energy, and since kinetic energy= ½*mass*velocity$^2$, the heavier mass ions will have slower velocities than the lighter mass ions as these ions pass through the drift region 70-3.

These particles are then detected by a detector 80-3 at the end of the drift region 70-3, and the instant in time when each particle arrives at the detector 80-3 is recorded as a multi-stop signal 170-3. By way of example but not by way of limitation, in the preferred embodiment, the detector 80-3 can be a Dual Microchannel Plate, #C-701, manufactured by R. M. Jordan Company. Other types of detectors 80-3 may be used in the invention by one of ordinary skill in the art in keeping within the scope of the invention. The information concerning the particles passes through the Multi-stop Time-to-Digital Converter (TDC) 100-3, and arrives at the computer/analyzer 40-3. Also, by way of example but not by way of limitation, in the preferred embodiment, the TDC 100-3 can be a TOF2 manufactured by Schmidt Industries, a division of SI Diamond Technology. Note that other similar devices may be substituted for the TDC 100-3 as used in the preferred embodiment and still keep within the scope of the invention.

The time it takes the particles to travel through the drift region 70-3 and impinge on detector 80-3 is compared against a time zero mark as determined by the time zero mark signal 150-3 received from the control electronics 20-3, and the time difference determines the mass of each of the desorbed particles. This time difference corresponds to the instant in time of a particular neutron pulse being emitted from the neutron generator 10-3 subtracted from the instant in time of an ion being detected at the detector 80-3, wherein the ion detected at the detector 80-3 was desorbed off the sample 50-3 due to the particular neutron pulse.

The time determination and comparison can be performed in the computer/analyzer 40-3, or any type of processor as otherwise convenient. As mentioned above, each time zero mark as determined by the time zero mark signals 150-3 are correlated to a corresponding one of the bursts of neutron pulses 120-3. The above-mentioned structure performs the TOF mass discrimination.

As described earlier, the californium source provides a significant primary ion yield, but is not actively controllable. The present invention uses a pulsed neutron generator to provide an adequate neutron flux to a suitable fissionable material. $^{238}$U is one such suitable fissionable material, since it has a relatively high n,f reaction cross section, which is approximately 1.2 barns for 14 MeV neutrons. Based on this, one can obtain reasonably high fission fragment yields. These fission fragment yields are strongly dependent on the neutron flux applied to the $^{238}$U by a neutron generator, which can be highly controlled by using current neutron tube technology.

One such neutron tube that can be used for implementing the present invention is a pulsed neutron tube developed by Martin Marietta Specialty Components, Inc., which can deliver neutron fluxes in a pulsed mode. In one embodiment, the neutron pulses would each cause about 10000 fission fragments due to a burst of approximately 5–100 nanoseconds. The burst repetition rate would be on the order of 2000 bursts/second. The burst repetition rate can be controlled by appropriate control signals 130-3 sent by the computer/ analyzer 40-3 to the control electronics 20-3. Based on the control signals 130-3 received, the control electronics 20-3 sends pulse out signals 160-3 to the neutron generator 10-3 at instants in time corresponding to the desired neutron pulse repetition rate.

Using an approach according to the invention, what previously took hours to perform mass spectrometry could be done in a manner of minutes or even seconds. The ion source would then be coupled to a TOF mass discriminator, allowing mass analyzing capability up to 100,000 amu, which is well beyond the range of current conventional mass spectrometers. The time zero mark for the TOF analysis can be derived from the electronics used to drive the neutron generator.

Another advantage of a system according to the invention is that all of the fission fragments generated would be synchronized. As a result, the background noise due to fission fragments that produce ions while the ions from the previous fission fragments are being analyzed can be eliminated, since these fission fragments associated with the background noise do not have a time mark associated with them.

While preferred embodiments of the invention have been described, modifications of the described embodiments may become apparent to those of ordinary skill in the art, following the teachings of the invention, without departing from the scope of the invention as set forth in the appended claims.

What is claimed is:

1. A system for studying a sample of material, comprising:
 a fission fragment generator comprising a pulsed neutron generator and a fissionable material having an n,f reaction cross-section greater than a predetermined value, said pulsed neutron generator being positioned at a first predetermined distance and at a first axial direction with respect to said fissionable material, so as to bombard said fissionable material with neutrons of a sufficient energy to cause heavy ions to be emitted from said fissionable material as fission fragments,
 wherein at least some of said fission fragments propagate toward and fall incident upon said sample of material positioned at a second predetermined distance and at a second axial direction with respect to said fissionable material, said first axial direction being different from said second axial direction, and
 wherein said at least some of said fission fragments induce desorption of said sample of material to produce secondary ions off of said sample of material; and
 a detector positioned at a third predetermined distance with respect to said fissionable material which is greater than said second predetermined distance, said detector configured to detect said secondary ions.

2. The system as recited in claim 1, wherein said pulsed neutron generator has an adjustable repetition rate for generating pulses.

3. The system as recited in claim 1, wherein said fission fragment generator is part of a heavy ion induced desorption mass spectrometer source.

4. The system as recited in claim 1, further comprising a time marker apparatus for marking times of pulses generated by said pulsed neutron generator.

5. The system as recited in claim 1, further comprising a correlation apparatus for correlating pulses emitted from said pulsed neutron generator with said desorption of said sample of material and said fission fragments produced from said fissionable material.

6. A system for studying a sample of material, comprising:
 a fission fragment generator comprising a pulsed neutron generator and a 238 isotope of uranium 238 ($^{238}$U) foil, said pulsed neutron generator being positioned at a first predetermined distance and at a first axial direction with respect to said $^{238}$U foil, so as to bombard said $^{238}$U foil with neutrons to cause heavy ions to be emitted from said $^{238}$U foil as fission fragments,
 wherein at least some of said fission fragments propagate toward and fall incident upon said sample of material positioned at a second predetermined distance and at a second axial direction with respect to said $^{238}$U foil, said first axial direction being different from said second axial direction, and
 wherein said at least some of said fission fragments induce desorption of said sample of material to produce secondary ions off of said sample of material; and
 a detector positioned at a third predetermined distance with respect to said fissionable material which is greater than said second predetermined distance, said detector configured to detect said secondary ions.

7. The system as recited in claim 6, wherein said pulsed neutron generator has an adjustable repetition rate for generating pulses.

8. The system as recited in claim 6, wherein said fission fragment generator is part of a heavy ion induced desorption mass spectrometer source.

9. The system as recited in claim 6, further comprising a time marker apparatus for marking times of pulses generated by said pulsed neutron generator.

10. The system as recited in claim 6, further comprising a correlation apparatus for correlating pulses emitted from said pulsed neutron generator with said desorption of said sample of material and said fission fragments emitted from said $^{238}$U foil.

11. The system as recited in claim 1, wherein said detector is positioned at a third axial direction with respect to said fissionable material which is approximately equal to said second axial direction.

12. The system as recited in claim 1, further comprising a grid positioned between said sample of material and said detector, said grid providing an electronic voltage for attracting said secondary ions as they are produced off of said sample of material, wherein a drift region is defined between said grid and said detector, and wherein a time it takes each of said secondary ions to traverse through said drift region to impinge on said detector determines a mass of said each of said secondary ions.

13. The system as recited in claim 12, further comprising:
 a time-to-digital converter coupled to said detector for determining when said each of said secondary ions impinge on said detector and to output a respective digital signal indicative thereof; and
 a control unit coupled to said fission fragment generator and said time-to-digital converter for providing control of said system, said control unit providing a first signal to enable said pulsed neutron generator to emit said neutrons at a first time, said control unit receiving said respective digital signal and configured to determine an amount of time between sending of said first signal and receiving of said respective digital signal, wherein said amount of time is directly related to a mass of one of said secondary ions corresponding to said respective digital signal.

14. The system as recited in claim 4, wherein said pulse neutron generator outputs a burst of said neutrons of between 5 nanoseconds and 100 nanoseconds, and wherein said burst of said neutrons causes about 10000 fission fragments to be emitted from said fissionable material.

15. The system as recited in claim 6, wherein said detector is positioned at a third axial direction with respect to said fissionable material which is approximately equal to said second axial direction.

16. The system as recited in claim 13, further comprising a grid positioned between said sample of material and said detector, said grid providing an electronic voltage for attracting said secondary ions as they are produced off of said sample of material, wherein a drift region is defined between said grid and said detector, and wherein a time it takes each of said secondary ions to traverse through said drift region to impinge on said detector determines a mass of said each of said secondary ions.

17. The system as recited in claim 16, further comprising:

a time-to-digital converter coupled to said detector for determining when said each of said secondary ions impinge on said detector and to output a respective digital signal indicative thereof; and a control unit coupled to said fission fragment generator and said time-to-digital converter for providing control of said system, said control unit providing a first signal to enable said pulsed neutron generator to emit said neutrons at a first time, said control unit receiving said respective digital signal and configured to determine an amount of time between sending of said first signal and receiving of said respective digital signal, wherein said amount of time is directly related to a mass of one of said secondary ions corresponding to said respective digital signal.

18. The system as recited in claim 6, wherein said pulse neutron generator outputs a burst of said neutrons of between 5 nanoseconds and 100 nanoseconds, and wherein said burst of said neutrons causes about 10000 fission fragments to be emitted from said $^{238}$U foil.

19. A system for studying a sample of material, comprising:

a fission fragment generator comprising a pulsed neutron generator and a fissionable material having an n,f reaction cross-section greater than a predetermined value, said pulsed neutron generator being positioned at a first predetermined distance with respect to said fissionable material, said pulsed neutron generator having an adjustable repetition rate for generating pulses of output neutrons, to establish a flux of said output neutrons in a direction towards said fissionable material to cause fission fragments to be ionized off of said fissionable material;

said sample of material being positioned at a second predetermined distance with respect to said fissionable material, said second predetermined distance being chosen such that a solid angle of dispersal of said fission fragments ionized off of said fissionable material results in at least a fixed percentage of said fission fragments falling incident on said sample of material, said at least a fixed percentage of said fission fragments inducing desorption of said sample of material to produce secondary ions off of said sample of material; and a detector positioned at a third predetermined distance with respect to said fissionable material which is greater than said second predetermined distance, said detector configured to detect said secondary ions;

a grid positioned between said detector and said sample of material, said grid being energized by a voltage so as to attract said secondary ions towards said grid;

a time-to-digital converter coupled to said detector for determining a first instant in time when said each of said secondary ions impinge on said detector and to output a respective digital signal indicative thereof;

a control unit coupled to said fission fragment generator and said time-to-digital converter, said control unit providing a first signal to enable said pulsed neutron generator to emit a burst of said output neutrons at a second instant in time when said control unit receives a control signal; and a computer coupled to said time-to-digital converter for receiving said respective digital signal and for outputting a control signal to said control unit, said computer determining an amount of time between said first instant in time and said second instant in time, wherein said amount of time is directly related to a mass of one of said secondary ions which was detected by said detector.

* * * * *